(12) United States Patent
Thorne

(10) Patent No.: US 6,293,946 B1
(45) Date of Patent: Sep. 25, 2001

(54) NON-STICK ELECTROSURGICAL FORCEPS

(75) Inventor: Jonathan O. Thorne, Boulder, CO (US)

(73) Assignee: Link Technology, Inc., Boulder, CO (US)

( * ) Notice: Subject to any disclaimer, the term of this patent is extended or adjusted under 35 U.S.C. 154(b) by 0 days.

(21) Appl. No.: 09/384,864

(22) Filed: Aug. 27, 1999

(51) Int. Cl.$^7$ .................................................. A61B 18/14
(52) U.S. Cl. .................................. 606/48; 606/51; 606/52
(58) Field of Search .................................. 606/45, 48–52

(56) References Cited

U.S. PATENT DOCUMENTS

| | | |
|---|---|---|
| Re. 34,432 | 11/1993 | Bertrand . |
| 3,685,518 * | 8/1972 | Beuerle et al. .......................... 606/51 |
| 3,920,021 | 11/1975 | Hiltebrandt . |
| 4,074,718 | 2/1978 | Morrison, Jr. . |
| 4,333,467 | 6/1982 | Domicone . |
| 4,492,231 * | 1/1985 | Auth ........................................ 606/51 |
| 4,593,691 | 6/1986 | Lindstrom et al. . |
| 4,783,368 | 11/1988 | Yamamoto et al. . |
| 4,823,791 | 4/1989 | D'Amelio et al. . |
| 4,869,745 | 9/1989 | Flaming . |
| 4,936,842 | 6/1990 | D'Amelio et al. . |
| 5,088,997 | 2/1992 | Delahuerga et al. . |
| 5,100,402 | 3/1992 | Fan . |
| 5,122,137 | 6/1992 | Lennox . |
| 5,151,102 | 9/1992 | Kamlyama et al. . |
| 5,152,762 | 10/1992 | McElhenney . |
| 5,156,613 | 10/1992 | Sawyer . |
| 5,196,009 | 3/1993 | Kirwan, Jr. . |
| 5,230,349 | 7/1993 | Langberg . |
| 5,244,462 | 9/1993 | Delahuerga et al. . |
| 5,256,138 | 10/1993 | Burek et al. . |
| 5,257,635 | 11/1993 | Langberg . |
| 5,382,703 | 1/1995 | Nohr et al. . |
| 5,395,363 | 3/1995 | Billings et al. . |
| 5,403,311 | 4/1995 | Abele et al. . |
| 5,423,814 | 6/1995 | Zhu et al. . |
| 5,437,662 | 8/1995 | Nardella . |
| 5,449,356 | 9/1995 | Walbrink et al. . |
| 5,507,744 | 4/1996 | Tay et al. . |
| 5,514,089 | 5/1996 | Walbrink et al. . |
| 5,542,945 | 8/1996 | Fritzsch . |
| 5,554,112 | 9/1996 | Walbrink et al. . |
| 5,562,659 | 10/1996 | Morris . |

(List continued on next page.)

FOREIGN PATENT DOCUMENTS

0246350 * 11/1987 (EP) ........................................ 606/51

OTHER PUBLICATIONS

Brady, George S., *Materials Handbook*, Fourteenth Edition, 1997, pp. 802–803
Merriamn, A.D., *A Concise Encyclopedia of Metallurgy*, 1965, pp. 942–943.
Permanco B.V.—Electrically Conductive Adhesives Technology, 2 pages.

*Primary Examiner*—Lee Cohen
(74) *Attorney, Agent, or Firm*—E. C. Hancock; F. A. Sirr; Holland & Hart LLP

(57) ABSTRACT

Electrosurgical forceps including two electrodes, each having a tip that is composed of a material that has the characteristics of electrical conductivity, high thermal diffusivity, and biocompatibility. Such characteristics allow the forceps to be used in medical applications to perform electrosurgery with a minimum of sticking to the tissue. These desired characteristics are found with pure silver and pure gold, as well as biocompatible alloys of silver and/or gold that are nearly entirely composed of silver and/or gold. The electrodes may include a thermal reservoir of this material spaced apart from a distal end of the electrode, with the thermal reservoir having a greater cross-sectional area than the distal end.

17 Claims, 4 Drawing Sheets

U.S. PATENT DOCUMENTS

| | | |
|---|---|---|
| 5,643,256 | 7/1997 | Urueta . |
| 5,647,871 | 7/1997 | Levine et al. . |
| 5,658,280 | 8/1997 | Issa . |
| 5,658,281 | 8/1997 | Heard . |
| 5,693,051 | 12/1997 | Schulze et al. . |
| 5,693,052 | 12/1997 | Weaver . |
| 5,697,926 | 12/1997 | Weaver . |
| 5,741,214 | 4/1998 | Ouchi et al. . |
| 6,059,783 | * 5/2000 | Kirwan, Jr. .......................... 606/51 |

* cited by examiner

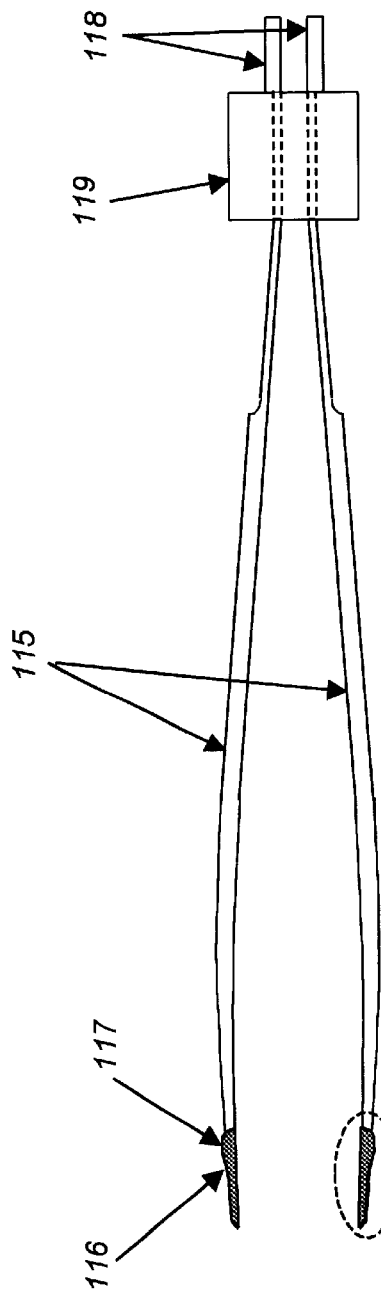
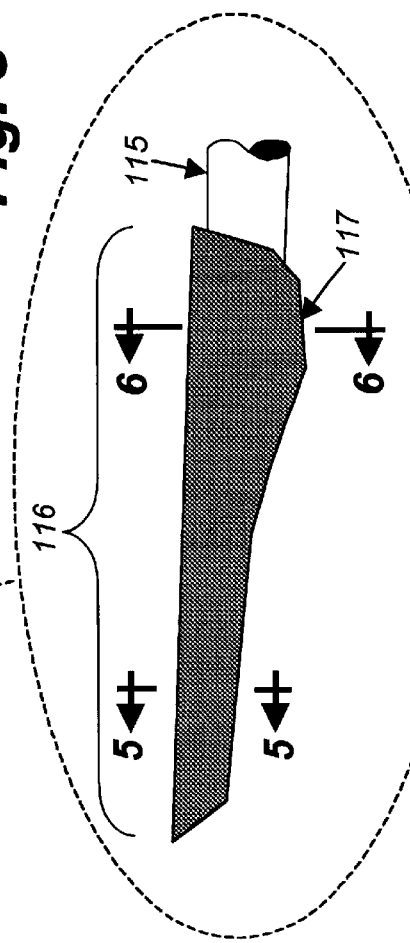
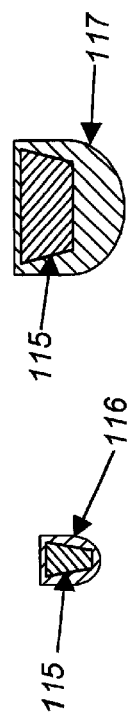
Fig. 3
Fig. 4
Fig. 5
Fig. 6

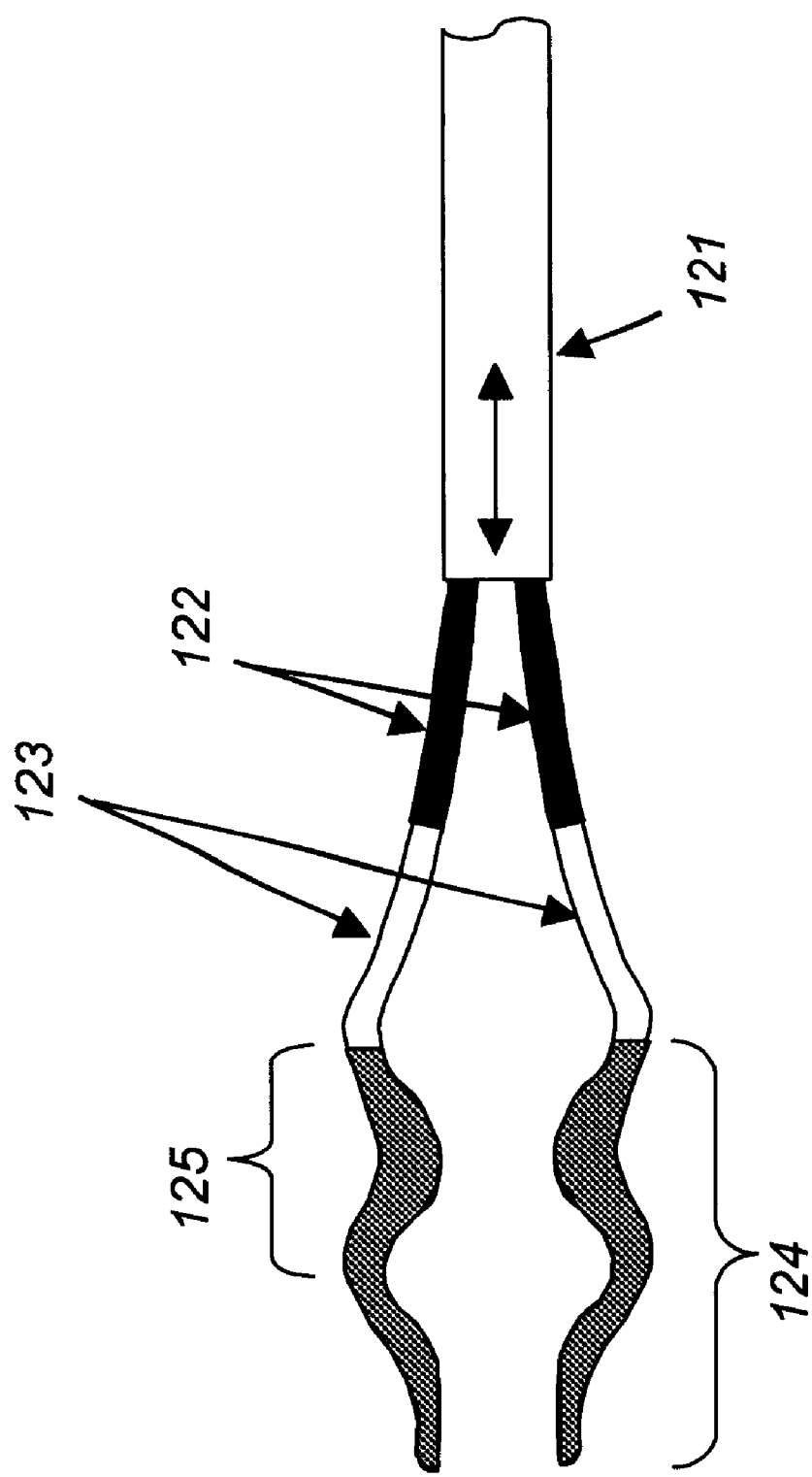

NON-STICK ELECTROSURGICAL FORCEPS

The present invention relates generally to electrosurgical apparatus including forceps or clamps, and more particularly, the present invention relates to electrosurgical forceps with non-stick characteristics.

BACKGROUND OF THE INVENTION

Electrosurgery includes the use of electrical energy in the form of alternating current at radio frequency (RF) levels to cut and/or coagulate biological tissue. The RF energy is typically produced by electrosurgical generators and applied to the tissue via electrodes that are electrically connected to the generator. The art of electrosurgical generators is well known. A variety of types of conventional electrodes have been employed for various types of electrosurgery in a variety of types of applications.

The use of conventional electrosurgical electrodes, however, is problematic in certain respects. For example, many electrosurgical electrodes cause arcing of electrical current between the electrode tip and the underlying tissue, rather than delivering the current in a uniform manner. Arcing may cause excessive tissue damage due to the large amount and density of the electrical energy transferred to the tissue via the arc of current. In addition, arcing causes conventional electrodes to develop hot spots at the point on the surface of the electrode where the arc contacts the electrode. These hot spots cause problems when they contact the tissue, because the tissue tends to stick to the hot spot. When the electrode is then moved or manipulated in any manner, the stuck portion of the tissue is pulled away from the surrounding tissue, causing further damage. Such sticking of the tissue to the electrode is a commonplace problem in surgery. This problem can be especially detrimental in precise surgical procedures. In particular, plastic, neurological, and gynecological surgical procedures are areas where sticking can often be harmful to patient outcome.

In order to reduce this sticking characteristic, electrodes with non-stick coatings have been developed. Unfortunately, the success of these coatings has been limited. Non-stick coatings of materials such as fluorinated hydrocarbon, silicon, and carbon have been used to coat the portion of the electrode that contacts the tissue. Such coatings are discussed in U.S. Pat. Nos. 4,785,807, 4,333,467 and 4,074,718, respectively. One problem with such coatings is the eventual breakdown of the coating over time due to the RF current flowing therethrough. Of course, once the coating detiorates, the non-stick characteristics do as well.

Materials with higher thermal conductivity, such as copper or copper alloys have also been used to reduce the sticking of tissue to electrodes. This is disclosed in U.S. Pat. Nos. 4,492,231 and 5,423,814. Copper, however, is not biocompatible, thus electrodes made of this material are not viable for medical use. Additionally, forceps with nickel tips have been used with some success to reduce sticking. This invention is disclosed in U.S. Pat. No. 5,196,009. While nickel is biocompatible and has a slightly higher thermal conductivity than stainless steel, which is traditionally used for forcep tips, sticking to nickel-tipped forceps still occurs.

It would therefore be desirable to provide improved electrode tips for use in electrosurgical techniques. Such electrode tips should be capable of applying radio-frequency energy evenly and uniformly to the tissue, without significant arcing or charring. In particular, the electrode tips should apply the radio-frequency energy without sticking so that damage to the tissue does not occur. The electrode tips should be usable with conventional electrosurgical power supplies and should have geometries which permit both accessibility to the patient target sites as well as providing the proper energy density and flux for performing coagulation and other conventional electrosurgical procedures.

In recent times, a split has developed between the medical communities in Europe and the United States. The desire to reduce the cost of medical supplies and, thus, medical procedures causes a portion of the medical community to embrace reusable medical supplies and instruments. Typically such items are sterilized with an autoclave, ethylene oxide gas, or other suitable technique, before re-use. Such reusable items must be able to withstand repeated sterilization through the autoclaving or other sterilization processes. In addition, reusable items need to be designed to withstand the wear and tear of repeated use. On the other hand, another portion of the medical community avoids reusable materials in order to reduce the likelihood of contaminating patients and medical personnel. In order to reduce such contamination, disposable items are used predominantly, or at least portions of the instruments and supplies are disposable. Some of the other reasons supporting reusables are that more expensive materials can be used in reusable supplies and instruments, when those more expensive materials have desirable characteristics, and also that the environmental impact of disposable items is so great.

U.S. Pat. No. 4,074,718 discloses an electrosurgical instrument with electrodes of increased thermal conductivity and a plurality of heat radiators attached thereto. Unfortunately, this reference did not recognize the importance of using bio-compatible materials, as several bio-compatible materials (silver and gold) were mentioned as interchangeable with non-compatible materials such as copper, aluminum, and beryllium. As to bio-compatibility at least, these materials are clearly not interchangeable, and they are probably not interchangeable in many other regards as well. In addition, the heat radiators on the electrode are poorly conceived, having a different effectiveness at different positional attitudes. Since the radiators rely on natural convection to remove heat from the electrode, the heat radiators will not function well when the electrode is oriented primarily vertically because the heat radiators will then be positioned above each other and heat convection away from the radiators will not easily occur. In addition, the embodiment with the ball electrode, shown in FIGS. 3 and 4 of this reference, will not conduct heat effectively to the radiators since there will be a bottleneck in the smaller diameter region between the ball and the heat radiators. Similarly, the embodiment shown in FIGS. 1 and 2 of this reference will not conduct heat effectively to the heat radiators because the electrode is a blade electrode having a relatively small cross-sectional area relative to its length which restricts the heat flow.

U.S. Pat. No. 5,423,814 discloses a bipolar coagulation device intended for endoscopic applications. While there is a discussion in this reference of the need to use metals having high thermal conductivity for the electrode materials, the disclosure is of an alloy of such materials, namely an alloy comprised roughly of 80% copper, 15% silver and 5% phosphorous. Unfortunately copper is not bio-compatible, and it is believed that phosphorous is not as well. A particular electrode shape intended to enhance heat transfer away from the electrode tip to reduce tissue sticking is disclosed in FIG. 9a of this reference. The conical shape disclosed may suffer from the drawback that there may be no adequate heat reservoir toward which to transfer the heat away from the tip. In addition the width of the conical shape near the tip will reduce the surgeon's visibility. It is desirable that the electrode block the surgeon's view of the surgical site as little as possible.

It has generally been believed by those in the medical industry that silver, while high in thermal conductivity, is not bio-compatible. Apparently this belief arose because people referring to silver usually, if not always, are referring to sterling silver. Sterling silver is an alloy composed of 92.5% silver and 7.5% copper. Since copper is clearly not bio-compatible, testing of sterling silver has shown it is not bio-compatible. In addition, pure silver is almost never used in any applications since it is so soft or ductile. This is one reason why sterling silver is used rather than pure silver. In addition, pure (or nearly pure) silver is not commonly available through supply channels.

It is against this background, and the desire to solve the problems of the prior art, that the present invention has been developed.

SUMMARY OF THE INVENTION

The present invention is directed to electrosurgical forceps including a pair of separate spaced-apart electrodes adapted for conducting electrosurgical current therebetween. Each of the pair of electrodes include a tip with a distal end and a thermal reservoir portion near the distal end, the thermal reservoir joining the electrode tip at a position spaced apart from the distal end. The thermal reservoir generally has a greater cross-sectional area than the cross-sectional area of the electrode tip to enhance the heat flow from the electrode tip to the thermal reservoir to reduce the temperature of the electrode tip during electrosurgery.

The present invention is also related to electrosurgical forceps including a pair of separate spaced-apart electrodes adapted for conducting electrosurgical current therebetween, wherein each of the pair of electrodes include a tip composed of a biocompatible material having a thermal diffusivity equal to or greater than $3.0 \times 10^{-5}$ m$^2$/s.

The tip may be composed of pure silver or a biocompatible alloy of silver. The tip may be composed of pure gold or a biocompatible alloy of gold. The electrode may include a thermal reservoir spaced apart from a distal tip of the electrode. The thermal reservoir may have a greater cross-sectional area than the distal tip of the electrode. The cross-sectional area of the electrode may remain substantially constant or increase from the distal tip to the thermal reservoir. The purity level of the tip may be over 97%, and it may be 99.95% or greater.

The present invention also relates to electrosurgical forceps including a pair of separate spaced-apart electrodes adapted for conducting electrosurgical current therebetween, wherein each of the pair of electrodes include a tip having a heavy coating or plating made of a biocompatible material with a thermal diffusivity equal to or greater than $3.0 \times 10^{-5}$ m$^2$/s.

BRIEF DESCRIPTION OF THE DRAWINGS

FIG. 3 is a side view of the electrosurgical forceps showing in phantom the electrical current path as well as detail of the tip section of the forceps.

FIG. 4 is an enlarged view of one of the tip sections of the electrosurgical forceps of FIG. 3.

FIG. 5 is a cross sectional view of the tip section of the electrosurgical forceps, taken along line 5—5 of FIG. 3.

FIG. 6 is a cross sectional view of the thermal reservoir contained within the tip section of the electrosurgical forceps, taken along line 6—6 of FIG. 3.

FIG. 7 is a side view of an alternate embodiment of the present invention.

DESCRIPTION OF THE SPECIFIC EMBODIMENTS

Figure 1:
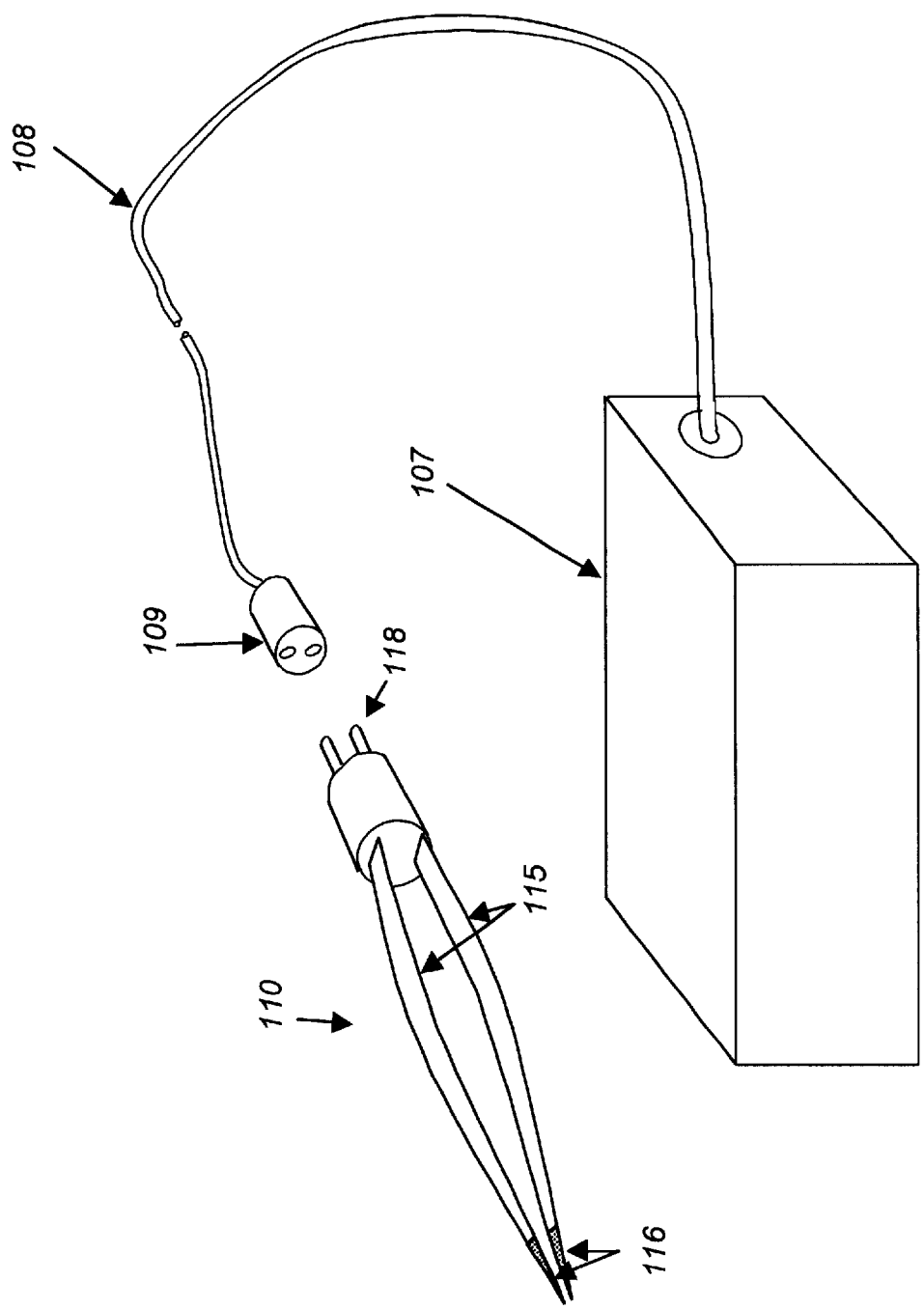
FIG. 1 illustrates an electrosurgical system comprising a conventional electrosurgical power supply a cable electrically attached to the supply and an electrosurgical forceps embodiment according to the present invention.

A biocompatible material with high thermal diffusivity and high electrical conductivity can be applied to bipolar electrodes, such as forceps. As stated above, in addition to sticking caused by heating of the overall electrode to an excessive temperature, sticking occurs due to localized hot spots caused by sparking or arcing between tissue and electrode during electrosurgery. This sparking can generate localized temperatures in excess of 1000° C. Even if the average electrode temperature is low, localized sticking due to hot spots from arcing can occur.

In order to achieve an effective non-stick electrode, the electrode must be designed to both control the overall temperature of the electrode and also quickly dissipate any localized hot spots caused by arcing. The invention disclosed prevents sticking to the forcep tips by accomplishing both control of overall temperature and dissipation of hot spots.

Control of temperature can be accomplished by creating a thermal reservoir. This is accomplished by having a sufficient mass of material with appropriately high heat capacity to prevent the electrode from reaching excessive temperatures. This thermal reservoir must be connected to the portion of the electrode that comes in contact with the tissue in such a way as energy can flow freely into the reservoir. Thus, cross sectional restrictions or insulative barriers between the thermal reservoir and the portion of the electrode that comes in contact with the tissue must be reduced or eliminated.

The ability of the electrode to dissipate heat from localized hot spots is a function of the thermal diffusivity ($\alpha$) of the electrode material in the region of the electrode where the sparking or arcing occurs. The higher the thermal diffusivity, the faster the propagation of heat is through a medium. The thermal diffusivity of a material is equal to the thermal conductivity (k) divided by the product of the density ($\rho$) and the heat capacity ($C_p$).

Thus $\alpha = k/(\rho \times C_p)$

The larger the thermal diffusivity, the shorter is the time required for the applied heat from a spark to penetrate into the depth of the electrode or dissipate.

The thermal diffusivity has units of length squared divided by time. Silver has been found to be an ideal material with which to form non-stick forcep tips. Silver has a very high thermal diffusivity of $16.6 \times 10^{-5}$ m$^2$/s. Silver in its purest form has also been found to be biocompatible. Gold also has a sufficiently high thermal diffusivity and is biocompatible. It has been found, however, that materials with thermal diffusivity of greater than $3 \times 10^{-5}$ m$^2$/s have improved non-stick qualities, however many of these materials, such as copper and aluminum, are not biocompatible. Materials such as nickel show slight improvement over stainless steel in non-stick characteristics, however, because of the low thermal diffusivity have insufficient non-stick qualities for many surgical procedures.

The thermal properties of various electrode materials are shown in Table I below:

TABLE I

| Material | HEAT CAPACITY $C_p \times 10^{-2}$ Joules/(Kg · ° K.) | THERMAL CONDUCTIVITY k W/(m · ° K.) | DENSITY $\rho$ kg/m$^3$ | THERMAL DIFFUSIVITY $\alpha \times 10^{-5}$ m$^2$/s |
|---|---|---|---|---|
| Silver | 2.39 | 415 | 10,500 | 16.6 |
| Gold | 1.30 | 293 | 19,320 | 11.7 |
| Copper | 3.85 | 386 | 8,890 | 10.27 |
| Aluminum | 9.38 | 229 | 2,701 | 9.16 |
| Tungsten | 1.34 | 160 | 19,320 | 6.30 |
| Nickel | 4.56 | 93.0 | 8,910 | 2.24 |
| Stainless Steel | 4.61 | 16.0 | 7,820 | 0.44 |

Referring now specifically to FIG. 1, electrosurgical forceps 110 constructed in accordance with the principals of the present invention can be used together with a conventional electrosurgical power supply 107 having an electrical cable 108 with a distal connector 109 connecting the electrosurgical forceps to the power supply. The electrosurgical power supply 107 may be any one of a variety of power supplies intended for electrosurgical cutting and/or coagulation. These power supplies are available from suppliers such as ConMed Corp., Utica, N.Y. and Valleylab, Inc., Boulder, Colo. Such power supplies are generally capable of operating at radio-frequencies of 500 kHz and at power levels of 1 watt to 300 watts. A particularly suitable power supply is commercially available from ConMed Corp., under the name Excalibur Plus PC™.

Figure 2:
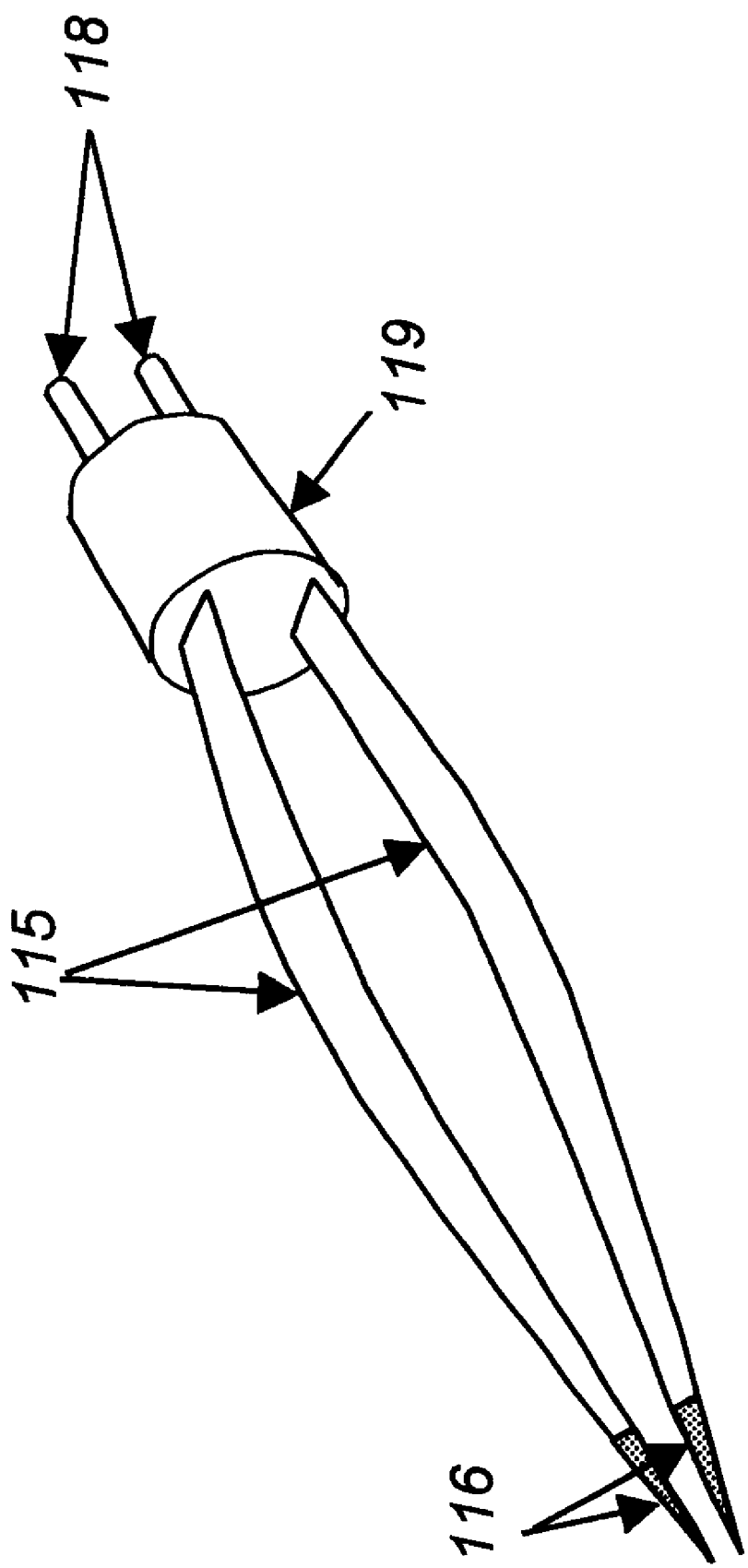
FIG. 2 is a detailed view of the electrosurgical forceps shown in FIG. 1.

As shown in FIG. 2, the electrosurgical forceps are comprised of a pair of blades 115 usually made of stainless steel. An insulator 119 maintains separation of the blades 115 and contains the portion of the blade that carries on the proximal end of the electrosurgical forceps.

In the preferred embodiment, silver or other material with a high thermal diffusivity is used as the tip material 116 of the forcep. Note that silver has the highest thermal diffusivity ($\alpha$) of all materials. Additionally, silver has the advantage that silver oxide is one of the few metal oxides that is electrically conductive. This means that the current flow will be relatively unimpeded by any small amount of oxide that is formed. Silver is very easy to burnish clean. Any material that does stick to the silver adheres very weakly, and wipes off easily. Most importantly, silver is biocompatible. The term biocompatible is used to refer to materials meeting the ISO 10993 standards for "Biological Evaluation of Medical Devices." Suitable materials for the electrode tip include silver or gold or a biocompatible alloy of silver or gold. Particularly preferred are suitably pure silver forcep tips having a purity of at least 80% silver by weight, more preferably of at least 99% by weight, and even more preferably, of 99.9% by weight. The remainder of the forcep tip would be composed of another biocompatible material.

Referring to FIG. 5, given that many materials with a high thermal diffusivity including silver are also somewhat ductile, a thin extension of the blade 115 normally made of stainless steel or other material with a high modulus of elasticity can be used in the tip for structural rigidity. This thin section of material is normally an extension of the blade 115 and is surrounded by the high thermally diffusive material of the tip 116.

FIG. 4 shows a detailed view of the tip section 116 of the forceps. FIG. 6 shows a portion of the tip section 116 that has an increased cross sectional area (relative to the distal end or head of the tip) to form a thermal reservoir 117. As discussed previously, this thermal reservoir 117 acts to minimize the overall temperature of the forcep tip thus reducing sticking of biological tissue to the tip. The tip section 116 can be either composed of a high thermal diffusivity material surrounding another material such as stainless steel or composed of solid high thermal diftusivity material.

In another embodiment of the invention, a clamp can be made using a similar tip configuration. This configuration can be used in a device commonly referred to by surgeons as Kleppinger forceps that are often used in gynecological surgery. These forceps are commercially available from Richard Wolf Instruments of Vernon Hills, Ill. Kleppinger forceps with the invention integrated into the forcep is shown in FIG. 7. Kleppinger forceps use a tube 121 that slides back and forth over the insulated portion of the forcep blades 122 causing the blades to clamp shut. In this embodiment of the invention a distal portion 124 of the blade 123 is composed of silver or other high thermal diffusivity substance that is biocompatible. An area of the distal portion 124 of the blades 123 is composed of enough silver that a thermal reservoir 125 is formed.

In either embodiment, the tip 116 or distal portion 124 is composed of a material having both high electrical conductivity and high thermal diffusivity and which is biologically compatible (bio-compatible) when used to apply radio-frequency energy to tissue and/or fusible materials. Preferably, this portion of the electrode will be formed from a substantially pure metal having the desired electrical and thermal characteristics. Suitable metals include silver and gold, or alloys of silver and gold. Particularly preferred are substantially pure silver electrode cores, preferably having a purity of at least 90% by weight, more preferably of at least 99% by weight, and even more preferably, of 99.9% by weight. The remainder of the electrode would be composed of another bio-compatible metal.

Alternatively, it is possible to employ a variety of composite, laminated, and coated structures as the electrode. For example, it would be possible to employ an aluminum central core which is coated with a coating of silver, gold, or tungsten, preferably silver. The coating of the outer metal should be relatively thick, typically having an annular thickness of at least about 0.01 inches, preferably in the range of 0.05 inches or more. The thickness of the coating is important because it is highly desirable for the coating to have a sufficient thickness and volume to allow heat to be conducted into the central area of the coating. This has at least two advantages. First, it is desirable to reduce the amount of heat on the outer surface of the electrode. Second, by having a substantial three-dimensional volume to the coating, it is easier for the heat to be conducted away from the tip of the electrode than if the coating were thin and had a smaller cross-sectional volume. The thickness of the coating is particularly important when the electrode core is composed of a material having a significantly lower thermal diffusivity than the coating, such as stainless steel.

The central core should be composed of a material having higher thermal conductivity than stainless steel, such as aluminum or copper. Even less preferably, carbon-coated stainless steel electrodes, such as those described in U.S. Pat. No. 4,074,718, could be used for performing the methods of the present invention. Such carbon-coated electrodes, however, do not display the optimum performance characteristics of the preferred pure metal, e.g. pure silver, electrodes.

It has been discovered that in coating a stainless steel electrode core with silver, it is much easier to coat the stainless steel if an acid etch is first used, followed by a strike layer of gold. The silver coating or layer can then be plated onto the gold strike layer slightly thicker than as it will exist in the final product. The thickness of the silver layer is then reduced slightly in finishing. Other suitable plating methods can also be employed.

One issue with such high purity levels of silver is the ductile nature of pure (or nearly pure) silver. Because of this, it is preferred to cold work-harden the silver by at least a 10% reduction in area in a conventional manner. Once work-hardened in this manner, the silver can be formed into a usable instrument such as the electrode of the present invention. Even more preferable is silver that has been work-hardened by a 50% reduction in area. Work-hardening has been found to not substantially affect the thermal conductivity of the material while making it much more resistant to damage.

The ability to transfer heat away from the tip of the electrode is an important advantage of the electrode assemblies of the present invention. The use of silver or gold (or other thermally conductive materials) as the core material (for solid electrodes) as well as the shape of the electrode are primarily responsible for the improved heat transfer. The heat transfer is further enhanced by the enlarged cross-sectional area of the core element. This enlarged cross-sectional area helps to promote the flow of heat away from the tip of the electrode, since the heat flow is proportional to the thermal conductivity of the metal, to the cross-sectional area of the region of interest, and to the temperature differential across the region of interest. The heat flow is inversely proportional to the length of the region of interest. As can be appreciated, this invention directly addresses the thermal conductivity and the cross-sectional area variables of the heat flow equation.

A factor controlling the overall width of the tip of the electrode is the need to preserve the surgeon's view of the surgical site while performing electrosurgery with the electrode. For this reason, the electrode tip is limited to a reasonable width and is connected to a thermal reservoir not too far away therefrom. In this manner, the visibility of the surgical site is maintained.

It can be appreciated that the silver or gold electrodes of the present invention can be autoclaved or subjected to other sterilization techniques and thus are suitable as reusable instruments. In addition, the particular insulating sleeves discussed above as well as the connector may be sterilized as well.

While the above is a complete description of the preferred embodiments of the invention, various alternatives, modifications, and equivalents may be used. Therefore, the above description should not be taken as limiting the scope of the invention which is defined by the appended claims.

The invention claimed is:

1. Electrosurgical forceps, comprising:
   first and second elongated and spaced-apart electrode arms adapted for conducting electrosurgical current there between during use in an electrosurgery procedure;
   said first elongated electrode arm having a tip portion that is spaced apart from a tip portion of said second elongated electrode arm;
   said first electrode arm having a first elongated metal core with said tip portion thereof having a first layer of a biocompatible metal with a thermal diffusivity equal to, or greater than, about $3.0 \times 10^{-5}$ m$^2$/s and with a layer thickness in the range of from about 0.01 to about 0.05-inch; and
   said second electrode arm having a second elongated metal core with said tip portion thereof having a second layer of a biocompatible metal with a thermal diffusivity equal to, or greater than, about $3.0 \times 10^{-5}$ m$^2$/s and with a layer thickness in the range of from about 0.01 to about 0.05-inch.

2. The electrosurgical forceps of claim 1 wherein said first and second elongated metal cores comprise stainless steel cores, and including strike-layers located intermediate said elongated metal cores and said layers of biocompatible metal.

3. The electrosurgical forceps of claim 2 wherein said strike layers are formed of a metal that is dissimilar to said stainless steel and said biocompatible metal.

4. The electrosurgical forceps of claim 3 wherein said strike layers are formed of gold.

5. The electrosurgical forceps of claim 1 including:
   first and second relatively large thermal reservoirs respectively formed as portions of said first and second layers of biocompatible metal.

6. The electrosurgical forceps of claim 1 wherein said biocompatible metal is selected from the group consisting of pure silver and pure gold.

7. The electrosurgical forceps of claim 1 said biocompatible metal has a purity level of at least about 97%.

8. The electrosurgical forceps of claim 1 wherein said biocompatible metal has a purity level of greater than about 99.95%.

9. The electrosurgical forceps of claim 1 wherein each of said first and second elongated metal cores are stainless steel, and wherein said first and second layers of biocompatible metal are selected from the group consisting of pure silver and pure gold.

10. The electrosurgical forceps of claim 9 wherein a purity level of said biocompatible metal is at least 97%.

11. The electrosurgical forceps of claim 9 wherein a purity level of said biocompatible metal is greater than 99.95%.

12. Electrosurgical forceps, comprising:
    first and second elongated and spaced-apart electrode arms adapted for conducting electrosurgical current there between during use in an electrosurgery procedure;
    said first elongated electrode arm having a tip portion that is spaced apart from a tip portion of said second elongated electrode arm;
    said first electrode arm having a first elongated metal core with said tip portion thereof having a layer of a biocompatible metal with a thermal diffusivity equal to, or greater than, about $3.0 \times 10^{-5}$ m$^2$/s and with a relatively large layer-thickness that is selected to allow heat generated during an electrosurgical procedure to be quickly dissipated throughout said layer-thickness; and
    said second electrode arm having a second elongated metal core with said tip portion thereof having a layer of a biocompatible metal with a thermal diffusivity equal to, or greater than, about $3.0 \times 10^{-5}$ m$^2$/s and with a relatively large layer-thickness that is selected to allow heat generated during an electrosurgical procedure to be quickly dissipated throughout said layer-thickness.

13. Electrosurgical forceps, comprising:
    first and second elongated and spaced apart electrode arms adapted for conducting electrosurgical current there between during use in an electro surgery procedure;
    said first elongated electrode arm having a tip portion that is spaced apart from a tip portion of said second elongated electrode arm;

said first electrode arm having a first elongated stainless steel core having a tip portion that is coated with a strike layer of gold followed by a layer of a metal selected from the group consisting of pure silver and pure gold that has a layer thickness in the range of from about 0.01 to about 0.05 inch; and said second electrode arm having a second elongated stainless steel core having a tip portion that is coated with a strike layer of gold followed by a layer of a metal selected from the group consisting of pure silver and pure gold that has a layer thickness in the range of from about 0.01 to about 0.05-inch.

14. The electrosurgical forceps of claim 13 including:

first and second relatively larger thermal reservoirs respectively formed as portions of said layer of said selected metal said first and second electrode arms.

15. Electrosurgical forceps, comprising:

first and second spaced apart electrodes;

each of said electrodes including a distal end tip adapted for conducting electrosurgical current during use in an electrosurgery procedure;

each of said electrodes having a thermal reservoir that is integrally formed with said tip of a corresponding electrode;

each of said thermal reservoirs being physically spaced apart from and closely adjacent to said tip of a corresponding electrode;

each of said thermal reservoirs having a greater cross-sectional area than a cross-sectional area of said tip of a corresponding electrode, to thereby enhance heat flow from each of said tips to a corresponding thermal reservoir, and to thereby reduce a temperature of said tips during an electrosurgery procedure;

each of said tips including a relatively strong metal core that is coated with a biocompatible material selected from the group consisting of pure silver and pure gold; and each of said thermal reservoirs being composed of a biocompatible material selected from the group consisting of pure silver and pure gold.

16. The electrosurgical forceps of claim 15 wherein:

each of said tips is composed of a biocompatible material selected from the group consisting of pure silver and pure gold having a purity level at least as high as about 97%.

17. Electrosurgical forceps, comprising:

first and second elongated and spaced apart electrode arms adapted for conducting electrosurgical current there between during use in an electro surgery procedure;

said first elongated electrode arm having a tip portion that is spaced apart from a tip portion of said second elongated electrode arm;

said first electrode arm having a first elongated stainless steel core having a tip portion that is coated with a metallic strike layer followed by a layer of a metal selected from the group consisting of pure silver and pure gold; and said second electrode arm having a second elongated stainless steel core having a tip portion that is coated with a metallic strike layer followed by a layer of a metal selected from the group consisting of pure silver and pure gold.

* * * * *